United States Patent [19]
Artzt et al.

[11] Patent Number: 6,158,277
[45] Date of Patent: Dec. 12, 2000

[54] PROCESS AND DEVICE FOR THE DETERMINATION OF THE TENDENCY OF COTTON TO ADHERE

[75] Inventors: Peter Artzt; Mehdi Azarschab, both of Reutlingen; Hans-Paul Schmid, Neuhausen, all of Germany

[73] Assignee: ITV-Institut fur Textil-und Verfahrenstrechnik, Denkendorf, Germany

[21] Appl. No.: 08/980,995

[22] Filed: Dec. 1, 1997

[30]    Foreign Application Priority Data

Dec. 7, 1996 [DE] Germany ............................ 196 50 945

[51] Int. Cl.[7] .............................. G01N 5/00; G01N 33/36
[52] U.S. Cl. ................................................................ 73/159
[58] Field of Search ........................................ 73/159, 160

[56]          References Cited

U.S. PATENT DOCUMENTS 3,290,929  12/1966  Sheldon ..................................... 73/160
3,815,178   6/1974  Goldman .................................... 19/205
4,135,276   1/1979  Handschuch et al. ..................... 19/204

FOREIGN PATENT DOCUMENTS 224873   8/1968   U.S.S.R. ................................. 73/159

*Primary Examiner*—Hezron Williams
*Assistant Examiner*—Willie Morris Worth
*Attorney, Agent, or Firm*—Dority & Manning

[57]          ABSTRACT

The invention relates to a process and to a device for the determination of the adhesion tendency of cotton by using cotton samples, whereby the sample taken from the material to be tested is opened down to the individual fiber as in the spinning process, and the fibers thus obtained are deposited on a testing surface under the influence of a certain centrifugal force in the form of a fiber ring. Following complete feeding of the sample, the deposited fiber ring is removed and the quantity of the fibers remaining caught on the testing surface is counted.

13 Claims, 3 Drawing Sheets

PROCESS AND DEVICE FOR THE DETERMINATION OF THE TENDENCY OF COTTON TO ADHERE

BACKGROUND OF THE INVENTION

The present invention relates to a process and a device to determine the tendency of cotton to adhere. In processing cotton, it has been a long-known problem to process sticky fibers as these adhere to each other in drafting and during the spinning process and also tend to form laps on the pressure rollers of the drafting equipment. There are several causes of this adhesion. The so-called "honeydew" which is deposited on the fibers of the open pods is a consideration. This is mainly a secretion of flies and other insects, but also micro-organisms assailing the cotton plant. There is however also the phenomenon whereby the cotton tends to adhere only during its processing. This adhesion is produced by crushed trash particles during ginning, i.e. when separating the cotton fibers from the seed grains.

Whatever the origin of this adhesiveness may be, the effect is however the same, resulting in difficulties in processing such fibers in the spinning process. It is therefore important for the spinning manufacturer to be able to ascertain already when purchasing the cotton whether or not it tends to adhere. Since the different kinds of cotton are mixed together after the harvest, and since the mixing is also a precondition in the spinning plant for a good yarn that meets its application requirements, the danger exists that cotton which tends to adhere may spoil the entire mixture. It is therefore especially important to find out preferably in the raw cotton whether a tendency to adherence exists, so that this fiber material may be eliminated in time or may be subjected to a special treatment by which this adhesion is removed, so that perfect cotton may in no case be mixed together with such cotton tending to adhere.

Lately in particular, the problem with cotton tending to adhere has taken a prominent importance since the fight against parasites has been more and more restricted for reasons of cost but also for ecological reasons. It is therefore especially important to recognize early this cotton which tends to adhere in order to prevent this affected fiber material from being mixed with perfect fiber material.

Different processes for the recognition and evaluation of the adhesion tendency of cotton have already become known. In the "Orcin" test for example, a color test is conducted with a chemical solution. The cotton samples to be thus tested are extracted in soxhlet apparatus with methanol. The methanol extract is taken up with water and is colored by adding the sulfuric acid orcin solution in function of the carbon hydrate contents. With a suitable concentration of the solution, color tones going from lemon yellow to dark red and brown are obtained, and these can be evaluated by colorimetric means. The different colors result from the total sugar concentration in the cotton sample.

With this method, suitable indications on the adhesion tendency of the cotton are obtained with the analogy process, but this test is very time consuming and requires expensive equipment, in particular if a large quantity of cotton samples are to be tested.

It is a further disadvantage that ratios have to be established each time between the photometric results and the experience gathered in operation with adhesion-prone cotton to ascertain to what degree a certain photometric result makes it possible to process the cotton, to process it under certain conditions, or whether unsustainable difficulties would result.

Another method to ascertain the adhesion tendency of cotton is the so-called "thermo-detection process". In order to obtain information on the behavior in process to be expected in the spinning plant, influenced by the adhesion tendency, the tendency of the cotton to adhere is simulated on metallic surfaces. Under the influence of heat and pressure upon the sample, the natural adhesion tendency is amplified and thus a longer exposure time is simulated. With this process, cotton flakes out of the bale and open cotton flakes and fiber slivers can be tested.

It is a disadvantage in this process that an expensive sample preparation is required. A uniform fleece in the format of the testing surface must be formed. The fleece is spread out on an aluminum film. Care must be taken so that the surface of the sample covers at least 95% of the testing surface. The sample spread out between aluminum films is finally placed on a pressing plate and is subjected to pressure and heat for 12 seconds. At the end of that period of time the heating plate must be lifted off immediately. This is followed by another two-minute pressing with the post-pressing device. The sample is then taken out of the device and, after a cooling period of at least 30 minutes, the upper film is carefully removed from the sample. The sample fibers which do not adhere on the aluminum film are carefully wiped off with a wiper by hand. The adhesion points remaining on the film, with adhering fiber bunches, are counted. Special conditions must also be adhered to for the counting in order to avoid counting mistakes. At least three individual tests must be made. If not at least two results fall into one adhesion tendency class and the third result into an adjoining class, the number of tests must be increased until two thirds of the test result can be assigned to one adhesion tendency class. Here, too, the disadvantage exists that this process is not only expensive, but that the relationship between the counting result and the experience of treatability must be established.

OBJECTS AND SUMMARY OF THE INVENTION

It is therefore a principal object of the present invention to create a process and a device which ensures a true-to-experience finding on the adhesion tendency of the cotton. Furthermore, the testing of raw cotton should be possible so that a mixing of adhering cotton with perfect cotton may be avoided as early as possible. Additional objects and advantages of the invention will be set forth in part in the following description, or may be obvious from the description, or may be learned through practice of the invention.

In the process according to the present invention, the cotton samples are separated down to single fibers and are placed on a testing surface without requiring any heat treatment or similar measure which is foreign to the spinning process. This testing method is extremely close to actual experience. An imitation of the spinning conditions is taking place and of the effects which occur in it, because only these are of interest for the spinning process. No relationships and analogies need be established between phenomena which have actually nothing in common with the spinning process. In addition, the process is simple and its implementation and even the evaluation can be automated, so that human influences are for the most part eliminated.

Additional details of the invention are explained through the drawings.

DETAILED DESCRIPTION

Reference will now be made in detail to the presently preferred embodiments of the invention, one or more examples of which are shown in the figures. Each example is provided to explain the invention, and not as a limitation of the invention. In fact, features illustrated or described as part of one embodiment can be used with another embodiment to yield still a further embodiment. It is intended that the present invention cover such modifications and variations.

Figure 1:
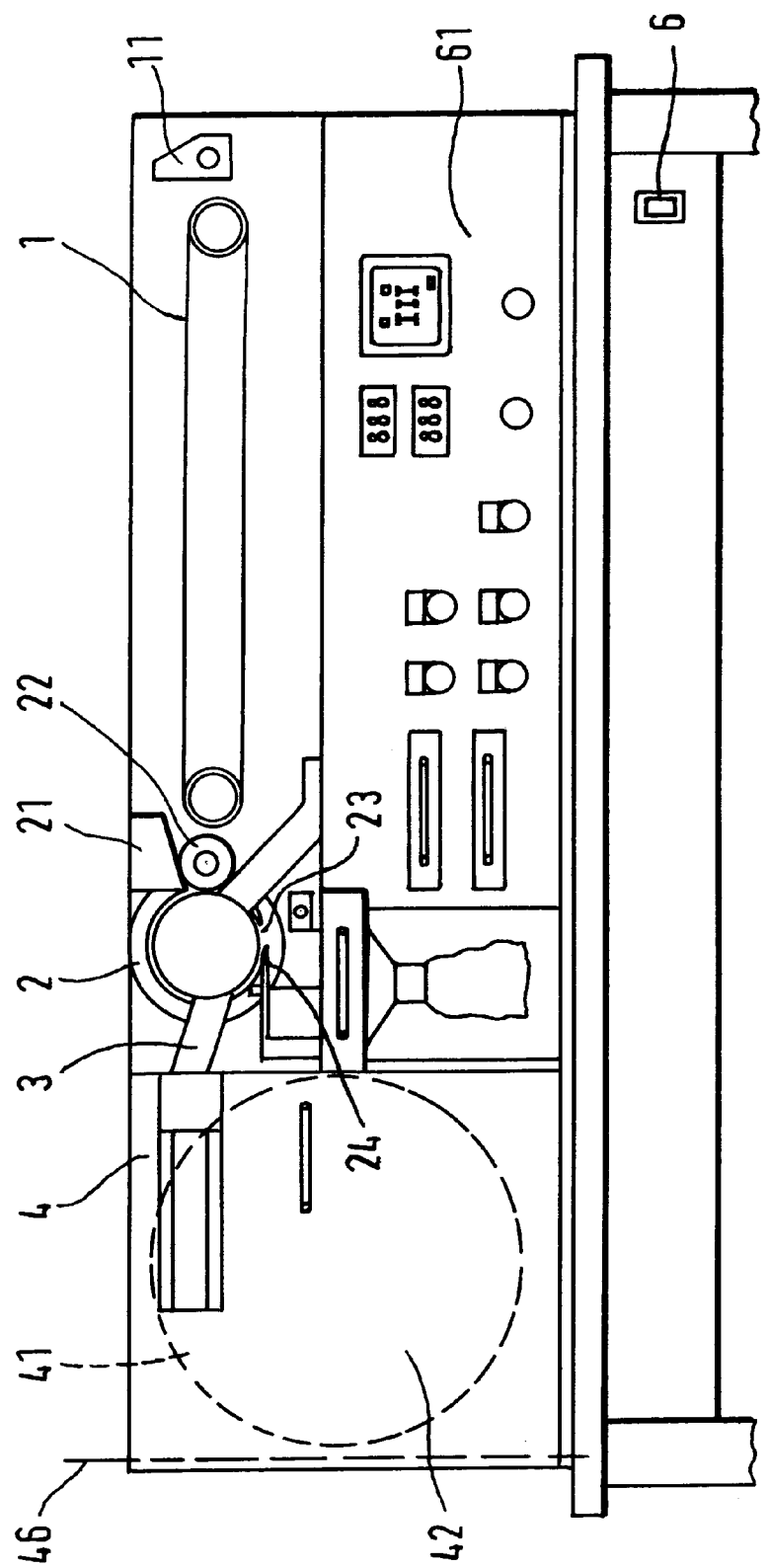
FIG. 1 shows the structure of the device to carry out the process according to the invention.
Figure 2:
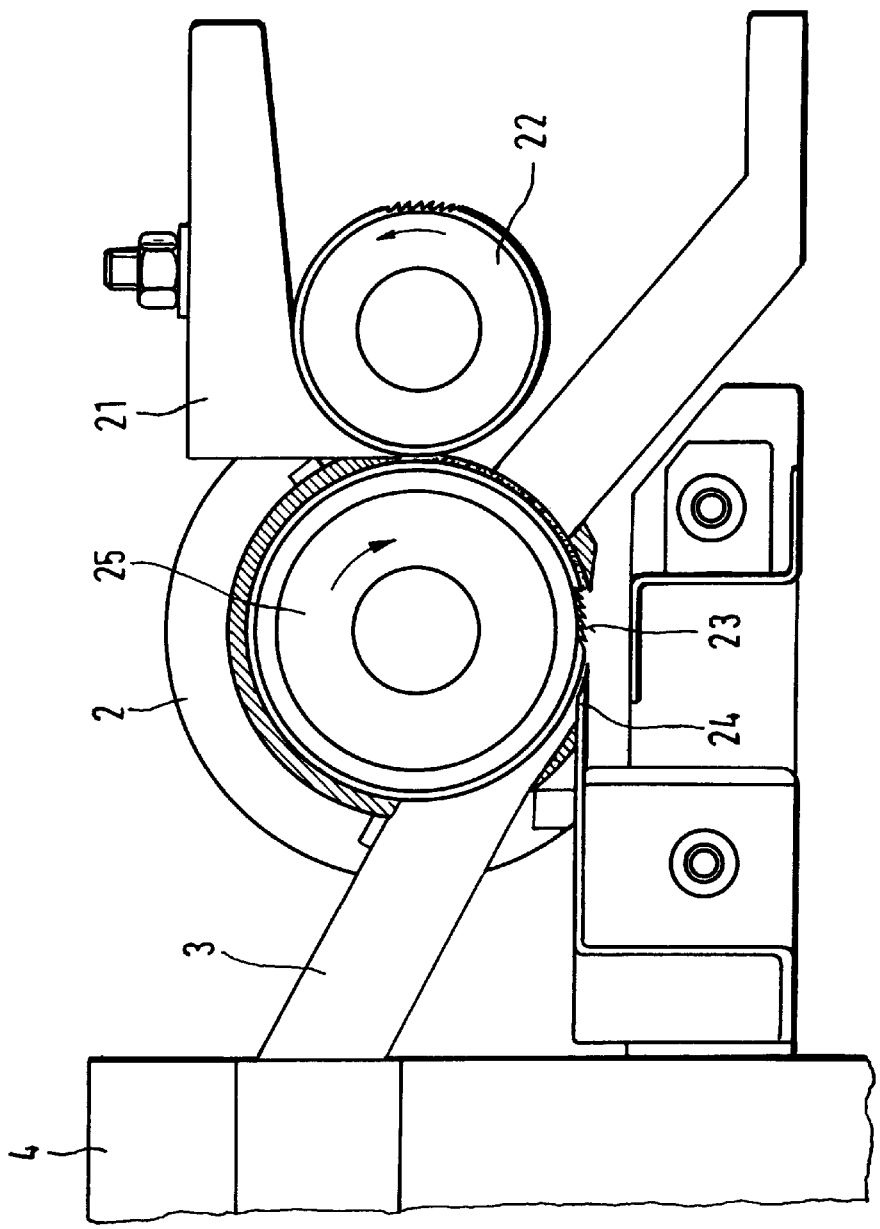
FIG. 2 shows the opener unit of the device according to FIG. 1.

In FIG. 1, the total structure of the device for the determination of the adhesion tendency of cotton is shown schematically. The cotton sample is placed on the feed conveyor belt 1 and is fed to the draw-in roller 22 which interacts with the draw-in trough 21. The fiber material is held back by the nip formed by the draw-in roller 22 and the draw-in trough 21, so that the opener roller 25 (FIG. 2) of the opener device 2 is able to detach individual fibers from the presented fiber tuft. For better retention, the draw-in roller 22 is covered with a saw wire clothing in which the teeth are inclined in a direction opposite to the direction of rotation. While the opener roller 25 rotates at high speed [approx. 8,000 r.p.m.], the drawing-in speed of the draw-in roller 22 is low [approximately 0.5 m/min] so that good opening down to the individual fibers may be achieved.

The fibers detached from the fiber tuft are conveyed past a trash elimination opening 23 to a fiber channel 3 through which the fibers are conveyed in an air stream into the testing surface unit 4. Depending on the position of the trash knife 24, trash elimination can be effected or can be omitted.

Figure 3:
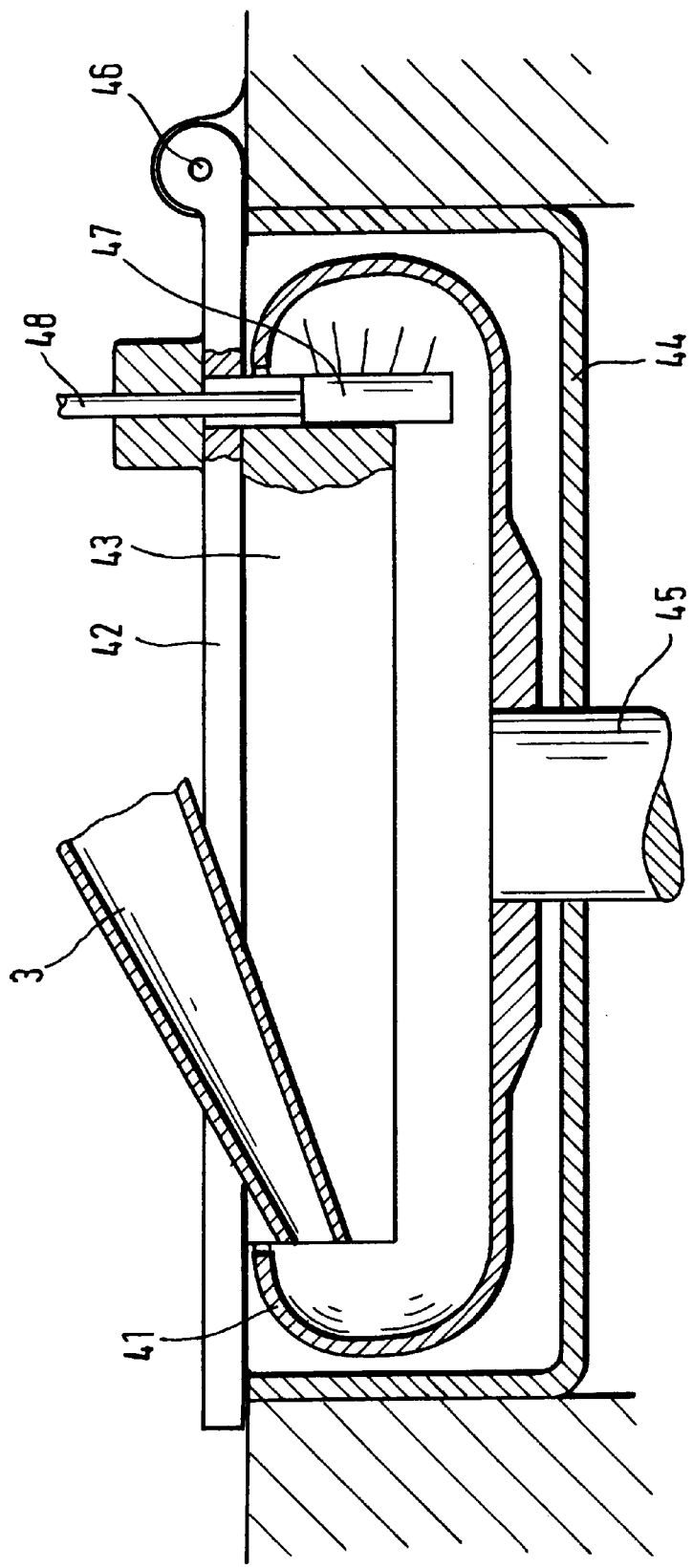
FIG. 3 shows the feed of the fibers to the testing surface 41 in detail.

The testing surface unit 4 is shown in detail in FIG. 3. The testing surface 41 itself is formed by the inside wall of a rotor which is mounted on shaft 45 and is driven via same. The testing surface 41 is located in a rotor housing 44 which can be closed by a housing cover 42 capable of swiveling around a hinge 46. The housing cover 42 is provided with an extension 43 which extends into the interior of the rotor while the housing cover 42 is closed and whose circumferential surface faces the testing surface 41. The fiber channel 3 lets out at the circumferential surface of the extension 43 and through it the fibers are guided from the opener device 2 to the testing surface 41. The testing surface 41 in the form of a rotor is advantageously made of a synthetic material. The testing surface 41 which comes into contact with the fibers is smoothed so that the fibers are able to glide over this surface without getting caught. The testing surface 41 is concave, so that the fibers fed through the fiber channel 3 accumulate into a ring on this testing surface 41. The testing surface 41 must be sufficiently large so that approximately 90% of the fibers of the sample to be tested may come into contact with the testing surface 41.

It has now proven to be advantageous if the testing surface 41 in the form of a rotor has a diameter of approximately 300 mm. In this way, a sliver length of 1 m is obtained when the fiber ring is opened. The width of the testing surface 41 is approximately 6 cm, so that the entire testing surface 41 measures 600 cm$^2$. If the sample weighs approximately 2 g/m, the necessary conditions for the testing surface 41 of 600 cm$^2$ are met.

With the rotation of the rotor at approximately 4,000 r.p.m. and with the sizes as indicated above, the fibers that are fed are subjected to a centrifugal force which amounts to approximately two thousand times the fiber weight. The centrifugal force presses the fibers against the rotor wall which is the testing surface 41. Upon feeding the entire amount of the sample, the rotor is stopped and the fiber ring which is thus produced is taken out of the rotor. Because the testing surface 41 is smoothed so that the fibers without adhesive characteristics do not cling to it, the rotor is empty after removal of the fiber ring, and no fibers remain. However if a sample is involved in which the fibers are affected by sticky substances, these will adhere to the testing surface 41 after the removal of the fiber ring. The quantity of the fibers left on the testing surface 41 is then a measure of the adhesion tendency of the cotton. To obtain this adhesion effect which is relevant for the spinning process on the testing surface, a certain minimum pressing force is necessary. In different tests it has been shown that with the dimensions of the testing surface 41 being as indicated above, a pressure force equal to approximately two thousand times the fiber weight is advantageously used in order to determine the adhesion tendency relevant for the spinning process.

As mentioned earlier, the quantity of the remaining fibers provides information on the adhesion tendency of the cotton. This quantity can be found by weight as well as by counting. The detection by counting is effected by counting the adhesion points, and this can be done manually as well as automatically. In FIG. 3, a sensor 47 is installed on the extension 43 across from the testing surface 41 and using it, the fibers which stand out as light against the black testing surface 41 can be counted. Such sensor devices are known, so that they need not be described here in further detail. The sensor 47 is mounted on a holding rod 48 so as to be capable of movement and can therefore be pulled back into the extension 43 so that the feed process may not be disturbed. On the other hand, the sensor 47 can be brought into the position across from the testing surface 41 which is optimal for counting. The sensor 47 can be connected directly to an evaluation device which evaluates the counting results.

When determining the adhering fiber quantity by weight, the fibers remaining after removal of the fiber ring are stripped from the testing surface and are weighed. The ratio of the weight of the adhering fibers and the sample weight in % is the measured magnitude of the adhesion tendency.

Climate is known to be an influence on the adhesion tendency of cotton during the spinning process. If the climate is modified, e.g. with respect to temperature or humidity in the testing process described above, it can easily be found whether the adhesion tendency of a cotton variety can be influenced by changing the climatic conditions. It may be found then that a cotton variety which has proven to be unsuitable for spinning under normal climatic spinning conditions, can still be found to be proper for spinning by changing the climatic conditions. The particularity of this process according to the invention lies in the fact that the spinning process is practically simulated, and that thus a direct relationship between the test results and the actual spinning conditions exist. No analogy between test results and experience parameters need to be established to begin with.

The process according to the invention can also be used to test cotton samples taken directly from the field, so that mixing with non-adhesive cotton may be prevented in time. In this case, it is however necessary to free the cotton fibers first of seed grains on a labor gin and to place the samples thus obtained on the feed conveyor belt. It is also possible to test fiber slivers which are placed on the conveyor belt directly. For this purpose, a sliver guide 11 is provided in addition.

Another variant of the process according to the invention consists in the fact that trash is eliminated upon opening by the trash elimination opening 23 and the trash knife 24. If the adhesion tendency can be traced to seed grains crushed on the gin, the sticky trash particles are then eliminated. It can thus be proven specifically whether the adhesion tendency is really only due to the fibers. Based on this test, appropriate measures can be taken in order to prevent the crushing of the seed grains.

The simplicity and direct analogy of the process make it possible to test cotton fiber material, be it in the form of raw cotton before ginning, or taken from bales, in form of flakes or as a fiber sliver, rapidly and easily. Thanks to the automated evaluation, human error in evaluation are also avoided.

It will be appreciated by those skilled in the art that various modifications and variations can be made in the present invention without departing from the scope of the invention. It is intended that the present invention include such modifications and variations as come within the scope of the appended claims and their equivalents.

We claim:

1. A process for determining the tendency of cotton to adhere in textile processing of the cotton, comprising opening a sample of the cotton with an opening device down to individual cotton fibers; conveying the opened cotton fibers from the opening device to a testing surface; depositing the opened fibers onto the testing surface under influence of a predetermined centrifugal force so that the opened fibers form a fiber ring on the testing surface; removing the formed fiber ring from the testing surface after a predetermined amount of the cotton sample has been opened and feed to the testing surface; and quantifying any fibers that have adhered to the testing surface after removal of the fiber ring as a measure of the cotton's tendency to adhere.

2. The process as in claim 1, wherein the entire cotton sample is opened and feed to the testing surface prior to removal of the fiber ring.

3. The process as in claim 1, further comprising rotating the testing surface at revolutions to achieve the predetermined centrifugal force, conveying the cotton sample to the opener device, and then conveying the opened fibers with an air stream via a fiber channel to the testing surface that is rotating.

4. The process as in claim 1, further comprising subjecting the individual opened fibers on the testing surface to a centrifugal force of about two thousand times the weight of the individual fibers.

5. The process as in claim 4, wherein the testing surface is a rotor with an attached shaft, and further comprising spinning the rotor at about 4,000 rpm via the shaft.

6. The process as in claim 1, wherein said step of quantifying the adhering fibers comprises determining a quantity of adhering fibers as a percentage of weight of the sample opened and fed as individual fibers to the testing surface.

7. The process as in claim 1, wherein said step of quantifying the adhering fibers comprises determining a quantity of adhering fibers by counting adhesion sites on the testing surface.

8. The process as in claim 1, wherein the cotton sample has a weight of about 2 g/m.

9. The process as in claim 1, further comprising varying climatic conditions in which said process is conducted and determining the effect of different climate conditions on the adhesion tendency of the cotton sample.

10. The process as in claim 1, further comprising removing trash from the opened fibers before depositing the fibers onto the testing surface.

11. An apparatus for determining the tendency of cotton to adhere in textile processing of the cotton, said apparatus comprising an opener device to open a cotton sample into individual fibers; a feed device disposed to deliver said cotton sample to said opener device, said opener device further comprising a draw-in roller, an opener roller, and a trash elimination opening; a testing surface and a fiber feeding channel disposed to deliver opened individual fibers from said opener device to said testing surface through the use of an air stream, said testing surface comprising a rotor mounted on and driven by a shaft; and means for counting fibers adhered to said testing surface as an indication of adhesion tendencies of the cotton after a predetermined amount of said cotton sample has been opened into individual fibers and deposited onto said testing surface with said rotor subjecting the fibers to a predetermined amount of centrifugal force so as to form a fiber ring on said testing surface.

12. The apparatus as in claim 11, wherein said means for counting fibers comprises a sensor device operationally disposed to detect adhered fibers in said testing surface.

13. The apparatus as in claim 1, wherein said rotor is formed of a synthetic material.

\* \* \* \* \*